(12) United States Patent
Zaloga et al.

(10) Patent No.: US 8,008,458 B2
(45) Date of Patent: Aug. 30, 2011

(54) FATTY ACID PHENOLIC CONJUGATES

(75) Inventors: Gary P. Zaloga, Fishers, IN (US); Rafat Siddiqui, Carmel, IN (US); William Stillwell, Indianapolis, IN (US)

(73) Assignee: Indiana University Health Inc., Indianapolis, IN (US)

( * ) Notice: Subject to any disclaimer, the term of this patent is extended or adjusted under 35 U.S.C. 154(b) by 309 days.

(21) Appl. No.: 11/691,816

(22) Filed: Mar. 27, 2007

(65) Prior Publication Data

US 2008/0004342 A1 Jan. 3, 2008

Related U.S. Application Data

(62) Division of application No. 10/742,295, filed on Dec. 19, 2003, now abandoned.

(60) Provisional application No. 60/435,319, filed on Dec. 19, 2002.

(51) Int. Cl.
*C07H 17/06* (2006.01)
*C07D 37/78* (2006.01)

(52) U.S. Cl. .................... 536/8; 549/403; 554/229

(58) Field of Classification Search ........ 536/8; 549/403; 554/229
See application file for complete search history.

(56) References Cited

U.S. PATENT DOCUMENTS

| | | | |
|---|---|---|---|
| 5,318,987 A | 6/1994 | Weithmann et al. | |
| 5,508,275 A | 4/1996 | Weithmann et al. | |
| 6,121,463 A | 9/2000 | Parker et al. | |
| 6,207,652 B1 | 3/2001 | Sakai et al. | |
| 6,225,338 B1 | 5/2001 | Romanczyk, Jr. et al. | |
| 6,235,294 B1 | 5/2001 | Perrier et al. | |
| 6,235,772 B1 | 5/2001 | Packer et al. | |
| 6,239,114 B1 | 5/2001 | Guthrie et al. | |
| 6,395,279 B1 | 5/2002 | Empie et al. | |
| 6,399,046 B1 | 6/2002 | Schonrock et al. | |
| 6,436,916 B1 * | 8/2002 | Guttag | 514/164 |
| 6,656,969 B2 * | 12/2003 | Young | 514/560 |
| 2005/0069551 A1 * | 3/2005 | Shoji et al. | 424/178.1 |

OTHER PUBLICATIONS

Daryugina, Elena I. et al., "Processing of Integrin $\alpha_v$ Subunit by membrane Type 1 Matrix Metalloproteinase Stimulates Migration of Breast Carcinoma Cells on Vitronectin and Enhances Tyrosine Phosphorylation of Focal Adhesion Kinase", *The Journal of Biological Chemistry*, vol. 277, No. 12, pp. 9749-9756 (Mar. 22, 2002).

Ingham, Kenneth C., "Molecular Interactions of Fibronectin", http://www.gwumc.edu/biochem/ingham/fnreview.htm (Dec. 12. 2003).

* cited by examiner

*Primary Examiner* — James Anderson
*Assistant Examiner* — Zohreh Vakili
(74) *Attorney, Agent, or Firm* — Woodard, Emhardt, Moriarty, McNett & Henry LLP

(57) ABSTRACT

This invention relates to a biologically active formulation containing a conjugate of a fatty acid and a complex phenol. The fatty acid can be selected from a variety of fatty acids including acids have between 12 and 24 carbon atoms. The phenol can be a polynuclear phenol, a polyphenol or a polyfunctional phenol having a variety of substituents. The formulation can include pharmaceutically acceptable carrier, including diluent. The formulation can be provided in an active dosage form suitable to inhibit mammalian cell growth and/or metastasis of malignant cells. The formulation can be used to induce cytotoxicity in mammalian cells particularly tumor cells or to treat and prevent cellular injury or dysfunction.

17 Claims, 14 Drawing Sheets

UV spectra of Resveratrol (RVT), and RVT-DHA conjugates A & B

Separation of propofol-DHA conjugate on a Thin layer Chromatograph (TLC).

Lane 1: Reaction Mixture with out propofol
Lane 2: Entire reaction mixture
Lane 3: DHA + propofol Absorption Spectra of propofol Absorption Spectra of propofol-DHA conjugate

GC analysis of propofol
Peak 1 & 3: Isomer of propofol (3%)
Peak 2: propofol (97%)

GC analysis of propofol-DHA conjugates
Peak 1: Propofol (40%)
Peak 2: Isomer of propofol (10%)
peak 3: DHA (50%)

Infra-Red analysis of propofol-DHA conjugate

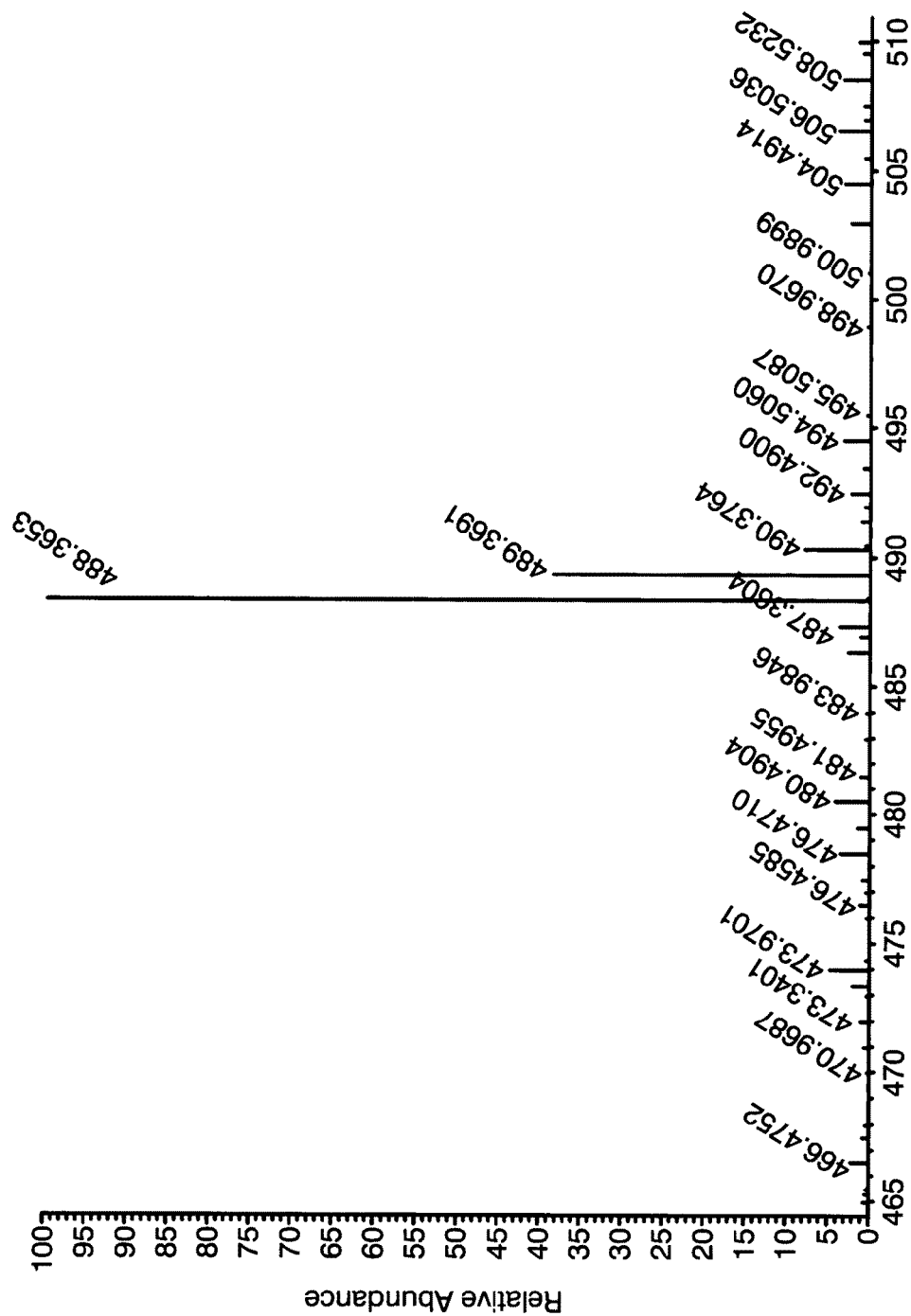
Fig. 7a Enlarged View of the box area from Figure 7

Fig. 12a-r

D= DHA
E= EPA
P= propofol
D+P= DHA and propofol
E+P= EPA and propofol
D-P= DHA-propofol conjugate
E-P= EPA-propofol conjugate

US 8,008,458 B2

FATTY ACID PHENOLIC CONJUGATES

CROSS REFERENCE TO RELATED APPLICATIONS

This application is a divisional of application Ser. No. 10/742,295 filed Dec. 19, 2003, now abandoned which claims the benefit of Provisional Application Ser. No. 60/435,319 filed Dec. 19, 2002, now abandoned which is hereby incorporated by reference in its entirety.

BACKGROUND OF THE INVENTION

The present invention is directed to a method of modulating cellular function and to a pharmaceutical composition containing a phenolic ester of a fatty acid selected to modulate cellular function.

Many drugs interact at the cell membrane surface by combining with cell surface receptors, or alternatively are taken into cells by specific transport systems. However, there are many drugs which, while they act within the cells by modifying one of many different functions such as DNA replication, actions of intracellular enzymes, or the activity of systems such as lysosomes or microtubules, are not able to penetrate cells very effectively. For example, there may be inadequate numbers or types of cell receptors and transport systems to which they can link or the systems may transport the drug into the cell, the mitochondria, or other nuclear membranes at less than optimum rates. This reduces or masks the activity of many potential drugs.

In addition, the cell membrane contains many precursors to bioactive substances, receptors, ion channels, and other proteins. Functions of these compounds are dependent upon membrane structure and properties. Substances, which alter membrane structure and function can modify cellular function.

In the light of the above problems, there continues to be a need for new and improved drugs to modulate cell functions, treat specific diseases, and increase the distribution, absorption, and biotransportation of drugs and other biologically active substances. The present invention is such an improvement and provides a wide variety of benefits and advantages.

BRIEF SUMMARY OF THE INVENTION

The present invention relates to a method of modulating cell function of mammalian cells, including modulation of cytotoxicity, cell replication and repair, cell injury, and cell signaling. The present invention also relates to a pharmaceutical formulation selected to induce such cellular response. Certain forms and features which are characteristic of the preferred embodiments are disclosed herein and are described briefly below as follows.

In one aspect the present invention provides a pharmaceutical formulation in dosage form selected to induce modification of one or more cellular functions. The pharmaceutical formulation includes a conjugate of a fatty acid and a phenol. More preferably, the pharmaceutical formulation includes a phenolic ester of a fatty acid. In preferred embodiments, the fatty acid is selected to include fatty acids having between about 12 and 24 carbon atoms. The fatty acid includes a hydrocarbyl group that can be a straight chain, a branched chain, or cyclic. Further, the hydrocarbyl group can be saturated, mono-unsaturated, and poly-unsaturated (conjugated or non-conjugated). The phenol can be provided as a polynuclear phenol, a polyphenol, and a polyhydridic phenol, each of which can be substituted with one or more pharmaceutically acceptable substituents or functional groups.

In another aspect the present invention is directed to a pharmaceutical formulation in dosage form that includes a conjugate of a fatty acid and a histidyl moiety or an imidazyl moiety. As listed above, the fatty acid can include a hydrocarbyl group that can be a straight chain, a branched chain, or cyclic. The hydrocarbyl group can be saturated, mono- or poly-unsaturated (either conjugated or not), and the hydrocarbyl group can be substituted.

In still yet another aspect, the present invention is directed to a method of treating mammalian cells, the method comprising administering to the cells a pharmaceutical formulation comprising either a fatty acid conjugate of a phenyl moiety or a fatty acid conjugate of a histidyl or imidazyl moiety in an amount effective to induce modulation of at least one cellular function in a portion of the treated cells. In a preferred embodiment, the present invention provides a method for inducing cytotoxicity in tumor cells including both benign and malignant cells. In other preferred embodiments, the present invention provides a method of modulating cellular replication and/or repair, and cell injury. In still yet other preferred embodiments, the present invention provides a method of altering cell signaling.

Further aspects, features, and advantages shall become apparent from the description and drawings contained herein.

DETAILED DESCRIPTION OF THE INVENTION

Figure 1:
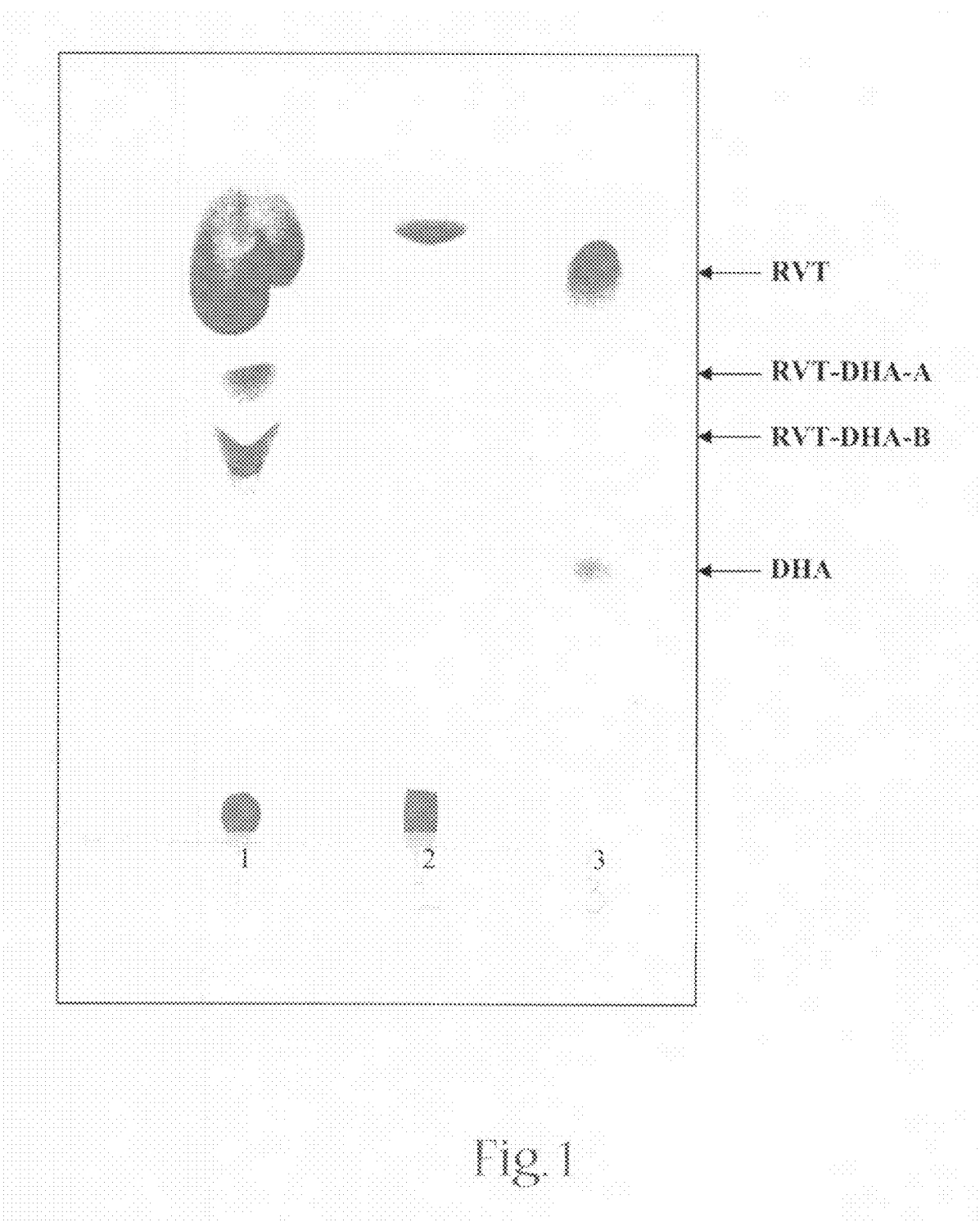
FIG. 1 is a scanned image of a TLC analysis of the esterification reaction of resveratrol and docosahexaenoic acid.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described formulations, treatment methods, and further applications of the principles of the invention as described herein are contemplated as would normally occur to one skilled in the art to which the invention relates.

In preferred embodiments, the present invention provides compounds and pharmaceutical formulations of a fatty acid conjugate of a phenolic moiety. In preferred embodiments, the compounds and pharmaceutical formulations of the present invention can be selected to modulate cellular functions including, but not restricted to: inducing cytotoxic activity, which can include selective cytotoxic activity against specific cells, the induction of apoptosis, and inhibition or reduction of tumor cell growth; and modulating cell replication, cellular growth, and/or a cell's response to injury. Additionally, preferred embodiments of the present invention can alter cell signaling.

In one form, the present invention includes biologically active compounds having a lipophilic component and a cytotoxic component. The lipophile component can be derived from a fatty acid, and the cytotoxic component can be derived from a phenolic derivative. In selected embodiments, the biologically active compound is a phenolic ester of a fatty acid. In other embodiments the biologically active compound is a conjugate of a fatty acid derivative and a phenol derivative connected via a bridge group.

Selected embodiments of the present invention exhibit increased transport or increased rate of transport of the biologically active compounds across lipid membranes which may be improved by linking them directly or indirectly to a lipid-soluble component. Fatty acids are examples of lipid soluble components. The fatty acids can absorb and/or pass through lipid-like materials such as membranes, cellular membranes, and membranes surrounding intracellular components such as a mitochondria and the nucleus. Many fatty acids are naturally occurring. These fatty acids can be combined (i.e., attached to a bioactive drug) and can transport the bioactive compounds into the cell at a much higher rate than would normally occur with the bioactive compounds in the absence of a fatty acid. The conjugation of the biologically-active component with a fatty acid can increase the cellular transport and/or membrane association for a wide variety of bioactive compounds including drugs, prodrugs, naturally occurring compounds, and their derivatives. Additionally, selected fatty acids exhibit selected bioactivity apart from their ability to facilitate binding bioactive components to membranes or transporting them across the membranes.

A number of diseases can be effected and treated by modulating basic cell function. A non restrictive list of potential diseases that can be treated according the present invention include diseases that affect the central nervous system, including Parkinson's disease and neuronal injuries, such as strokes; cardiac diseases include myocardial infarction, heart failure, and arrhythmia; and pulmonary diseases, including inflammatory lung disease such as acute respiratory distress syndrome. Other potential areas in which the present invention can contribute for treatment and/or cure include arthritis, cancers and wound repair.

The fatty acid component can include a long chain, alkyl-substituted fatty acid. The fatty acid component preferably includes greater than 12 carbon atoms and more preferably between 12 to 24 carbon atoms. The alkyl chain can be a straight chain, a branched chain, or cyclic chain, all of which can be, mono- or polyunsaturated, (conjugated or non-conjugated), and combinations thereof.

In other preferred embodiments, the fatty acid includes naturally occurring fatty acids; more specifically the ω-3 long chain polyunsaturated fatty acids. Referenced examples of fatty acids for use in the present invention include, but are not restricted to: lauric acid (n-dodecanoic acid), myristic acid (n-tetradecanoic acid), palmitic acid (n-hexadecanoic acid), stearic acid (n-octadecanoic acid), arachidic acid (n-eicosanoic acid), behenic acid (n-docosanoic acid), lignoceric acid (n-tetracosanoic acid), palmitoleic acid (cis-$\Delta^9$-hexadecenoic acid), oleic acid (cis-$\Delta^9$-octadecenic acid), linoleic acid (cis, cis-$\Delta^9,\Delta^{12}$-octadecadienoic acid, cis, trans-$\Delta^9,\Delta^{11}$-octadecadienoic acid, and trans, cis-$\Delta^{10}$, $\Delta^{12}$-octadecadienoic acid), linolenic acid (cis-$\Delta^9,\Delta^{12}$, $\Delta^{15}$-octadecatrienoic acid, cis, trans, cis-$\Delta^9,\Delta^{11}$, $\Delta^{13}$-octadecatrienoic acid, cis, trans, trans-$\Delta^9,\Delta^{11},\Delta^{13}$-octadecatrienoic acid, and trans, trans, cis-$\Delta^9,\Delta^{11},\Delta^{13}$-octadecatrienoic acid), and arachidonoic (cis-$\Delta^5,\Delta^8,\Delta^{11},\Delta^{14}$-eicosatetraenoic acid), docosahexanoic acid (DHA), and eicosopentenoic acid (EPA).

The phenolic component can be selected from a polynuclear phenol, a polyphenol substituent, a polyhydridic phenol, and polysubstituted phenol. Selected phenols exhibit biological activities, especially cytotoxic activity against specific cell lines, including anti-tumor activity against either benign or malignant cells, anti-neoplastic activity, and anti-cell growth activity.

Phenols are a class of chemical components that include an aromatic ring with a hydroxyl group. Various phenols exhibit wide-ranging biological activity. Specific phenols have been shown to exhibit anti-oxidant and anti-carcinogenic activity and modulate inflammatory responses such as sepsis, acute respiratory failure, inflammatory bowel disease, arthritis, and other inflammatory diseases. Some of these substances can exhibit cardio-protective activities that include anti-arrhythmia, anti-arteriosclerotic effects, and prevention of loss of cardiac contractile function in patients with heart disease. Additionally, the phenolic derivatives can exhibit cell protective effects including repair after non-lethal cellular injury. The phenols can be classified into different subcategories. The subcategories include simple phenols, polynuclear phenolic species, polyphenol species, polyhydric phenols, and other substituted phenols. Simple phenols include a single aromatic ring with a hydroxyl substituent; a more complex phenol includes additional substituents. Polynuclear phenols include multiple (two or more) conjugated aromatic ring systems, such as genistein and resveratrol.

Polyphenols, as this term is used herein, are considered to include one or more phenols bonded together through one or more linking groups. Examples of polyphenols include resveratrol, catechins, flavonoids, and alpha-tocopherol, to name just a few. In each of the above subcategories, the phenols can include additional functional groups. For example, the phenols can include two or more hydroxyl groups, i.e., polyhydridic phenols. More complex phenols for use in the present invention include other substituents including alkyl groups. The alkyl groups can be provided as a straight chain, a branched chain, cyclic and/or aromatic; further, the alkyl group can also be saturated or unsaturated, conjugated or not. Additionally, the phenols and the alkyl groups can be substituted with one or more of: amides (—C(O)NRR'), amino (—NH$_2$), secondary amino (—NRH), tertiary amino (—NRR'), esters, ethers (—OR), halogens (i.e., fluoro (F$^-$), chloro (Cl$^-$), bromo (Br$^-$), iodo (I$^-$)), hydroxyl (—OH), oxygen, nitrogen, sulfonyl (—SO$_2$—), thiols, (—S—), thiolates, and thionyl (—SO—) substituents.

Selected examples of phenols for use in the present invention include: propofol (2,6-diisopropylphenol), butylated hydroxytoluene, resveratrol, and vitamin E.

The phenol-fatty acid conjugate can be prepared under conditions suitable for ester formation. Various methods are known to those skilled in the art. Preferred methods include forming a more active intermediate (reactive ester, anhydride, or amide) of the fatty acid and reacting that highly reactive intermediate with the phenol in the presence of a non-nucleophilic base. The resulting product can be isolated using techniques known to those skilled in the art.

In another form, the present invention can include pharmaceutical formulations having a lipophilic component and a histidyl or imidazyl component. The lipophilic component is as described above. The histidyl or imidazyl component can be conjugated with the fatty acid through an amide linkage.

The pharmaceutical formulation for use in the present invention can also include pharmaceutically-acceptable auxiliaries, including diluents, carriers, excipients, buffering agents, wetting agents, emulsifiers, lubricants, and antioxidants. Further, the pharmaceutical formulation can include incorporating one or more active components in a liposome or lipid vesicle.

As used herein, the term "pharmaceutically acceptable carriers" means a non-toxic, inert solid, semi-solid or liquid filler, diluent, encapsulating material or formulation auxiliary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. Examples of pharmaceutically acceptable. antioxidants include—water soluble antioxidants such as ascorbic acid, cysteine hydrochloride, sodium bisulfite, sodium metabisulfite, sodium sulfite, and the like; oil soluble antioxidants such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

By use of the "term effective amount" includes a sufficient amount of the phenol ester of a fatty acid or conjugate of the phenol and fatty acid to elicit the desired result, i.e., the desired pharmacological or biochemical result over the amount in which no result is observed. In preferred embodiments, the effective amount of the phenol ester to induce cytotoxic activity is an amount of greater than or equal to about 10 micromolar. More preferably the effective amount to induce cytotoxic activity is between about 25 and about 50 micromolar.

In other embodiments, the formulations of the present invention can be used to inhibit metastasis of malignant cells or malignant growths to a secondary invasion site. It is thought that in one form, the formulations of the present invention can inhibit malignant cells by disrupting the cell signaling mechanism or effecting the detachment of the malignant cells from the primary invasion site; circulating through the vascular system or once the malignant cells are in the vascular system inhibiting these cells from attaching to other tissue or other sites to propagate secondary growths.

In one preferred embodiment, effective amount of the phenol ester to inhibit metastasis is an amount of greater than or equal to about 10 micromolar. More preferably the effective amount to inhibit metastasis is between about 25 micromolar and about 50 micromolar.

For the purpose of promoting further understanding and appreciation of the present invention and its advantages, the following examples are provided. It will be understood, however, that these examples are illustrative and not limiting in any fashion.

Example 1

Synthesis of Resveratrol Ester of Docosahexaenoic Acid

The synthesis of the resveratrol ester of docosahexaenoic acid was performed in two steps. In the first step, the docosahexaenoic-anhydride was synthesized, and in a second step this anhydride was coupled to resveratrol.

Figure 2:
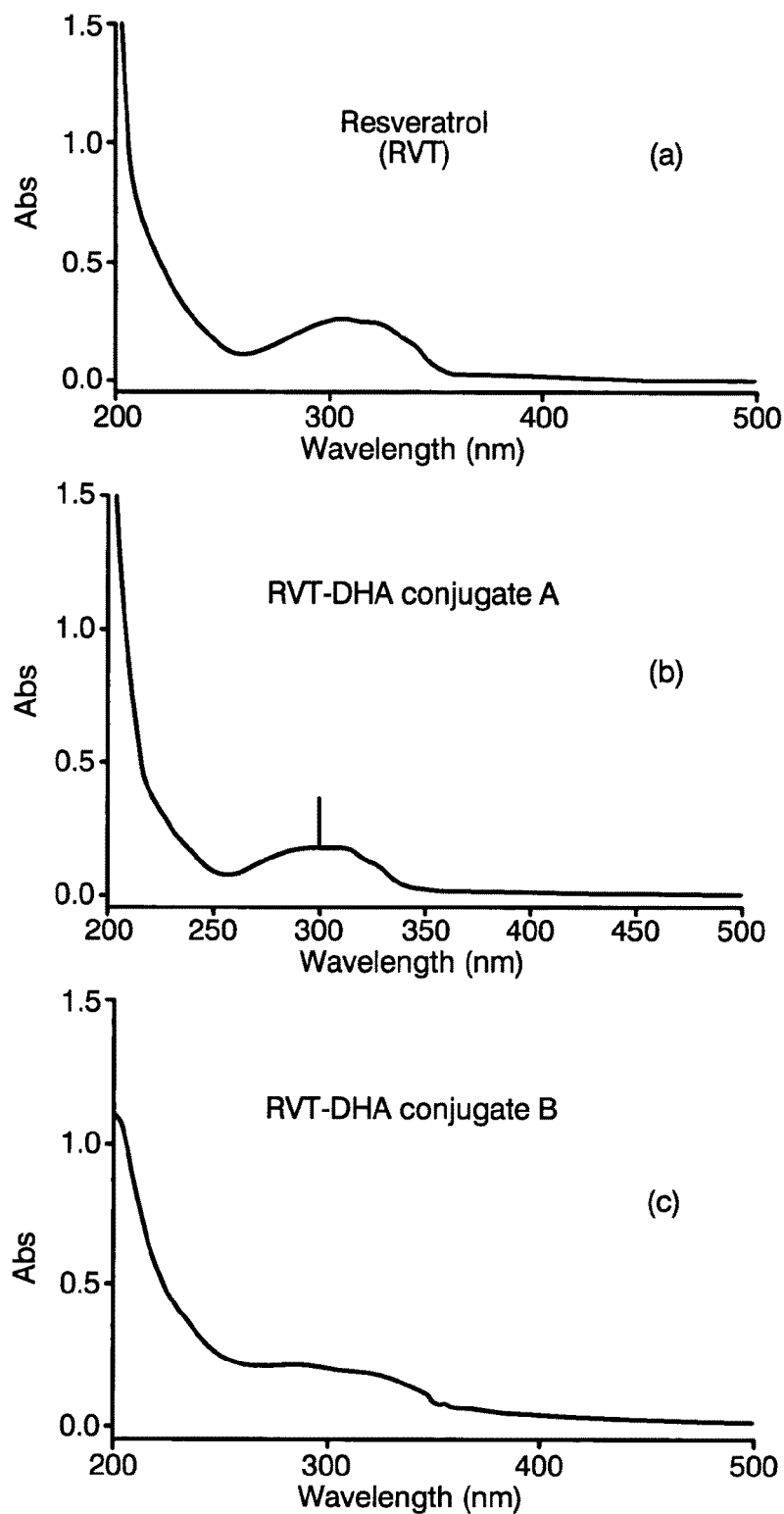
FIG. 2 is a scanned image of the UV spectrogram for the resveratrol and docosahexaenoic acid conjugate prepared according to the procedure described in Example 1.

For the initial step to form the anhydride, docosahexaenoic acid (DHA, 0.19 µM), dicyclohexylcarbodiimide (DCC, 0.145 µM), and the anti-oxidant butylated hydroxytoluene (BHT, 1.5 µM) were dissolved in 4 mls of dimethylformamide (DMF) and mixed for one hour at room temperature under an atmosphere of nitrogen. In the second step, resveratrol (RVT) (0.095, µM) and 4-dimethylaminopyridine (DMAP, 0.095 µM) were then added to the DHA-anhydride mixture. The resulting solution was stirred at room temperature under an atmosphere of nitrogen for about 17 hours. The reaction product was filtered, washed with chloroform, and then separated by analytical thin layer chromatography (TLC). The TLC plate was developed with a methylene chloride/ethyl ether/acetic acid (80/20/1, v/v/v). The reaction products were visualized on the TLC plate using iodine and ultraviolet (UV) absorbence. Although there were five possible reaction products (RVT includes three hydroxyl substituents), the initial analysis of the developed TLC plate revealed that only two products were produced in substantial quantities. (See FIG. 1.) The two products had Rfs of about 0.50 and 0.55 using the eluent system described above. The species having an Rf equal to about 0.50 was isolated from the TLC plate and analyzed using UV spectroscopy. The UV spectra is illustrated in FIG. 2 and indicates the presence of both DHA and RVT in the isolated product. The formation of the DHA-RVT ester was further verified by hydrolyzing the previously isolated product with a sodium hydroxide. The hydrolysis yielded 2 products: one was identified as DHA and the other was identified as RVT based upon their Rf values on a TLC plate. The molecular weight of the reaction product was roughly estimated based upon the UV spectra. This reaction product was further tested on Jurkat cells.

Example 2

Synthesis, Purification and Characterization of 2,6 Diisopropylphenyldocosa-Hexaenoate (Propofol-DHA)

Synthesis

To minimize auto-oxidation, all procedures were performed in reduced light and under nitrogen. The reaction was carried out in two steps: synthesis of docosahexaenoic acid anhydride (DHA-anhydride), subsequently followed by the esterification of DHA by 2,6 diisopropylphenol(propofol).

DHA (100 mg, 0.305 mmol), a coupling reagent, N,N'-dicyclohexylcarbodiimide (94 mg, 0.450 mmol), and an anti-oxidant, 2,6 di-tert-butyl-4 methylphenol (BHT) (5 mg) were dissolved in 5 ml of chloroform. The reaction was stirred for 60 min at room temperature. propofol (49.8 mg, 0.28 mmol) and 4-(dimethyl amino) pyridine (18.5 mg, 0.152 mmol were then added to the reaction. The resulting mixture was stirred for a period of 12 hours; the reaction suspension was then filtered and washed with petroleum ether and subjected to purification.

Purification

The product of the reaction was purified on an analytical thin layer plate (Silica Gel, 60 A, 0.2 mm thickness); the plate was developed in a solvent mixture of Petroleum Ether/Ethyl Acetate (92/8, v/v), and the products were visualized by iodine vapor. The result was compared to the control, which contained the entire reaction mixture without propofol.

Figure 3:
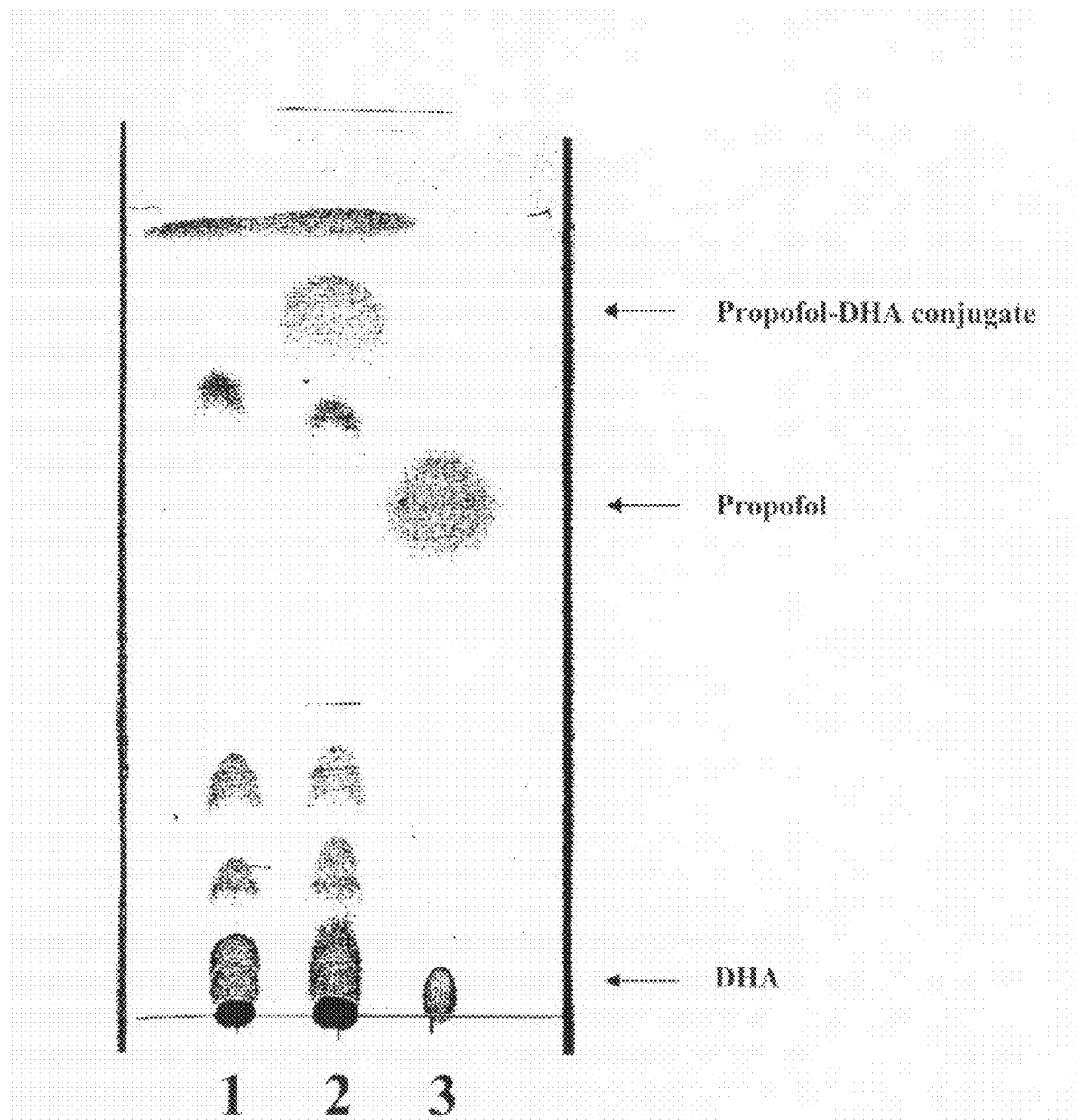
FIG. 3 is a scanned image of a thin layer chromatography plate used to analyze the reaction mixture containing propofol and docosahexaenoic acid.

As compared to the control, a new product was formed (See FIG. 3, illustrating the thin layer chromatographic analysis of the reaction mixture) with a Rf value=0.90. In FIG. 3, lane 1 is the reaction mixture without propofol; lane 2 is the entire reaction mixture; and lane 3 is unreacted DHA and propofol. The band corresponding to the new compound was scraped off the TLC plate, suspended with chloroform/methanol (20/80, v/v), passed through a glass filter, and subjected to characterization.

Characterization

The characterization of the compound was performed by the combination of techniques described bellow:

a) Absorption Spectra

Figure 4A:
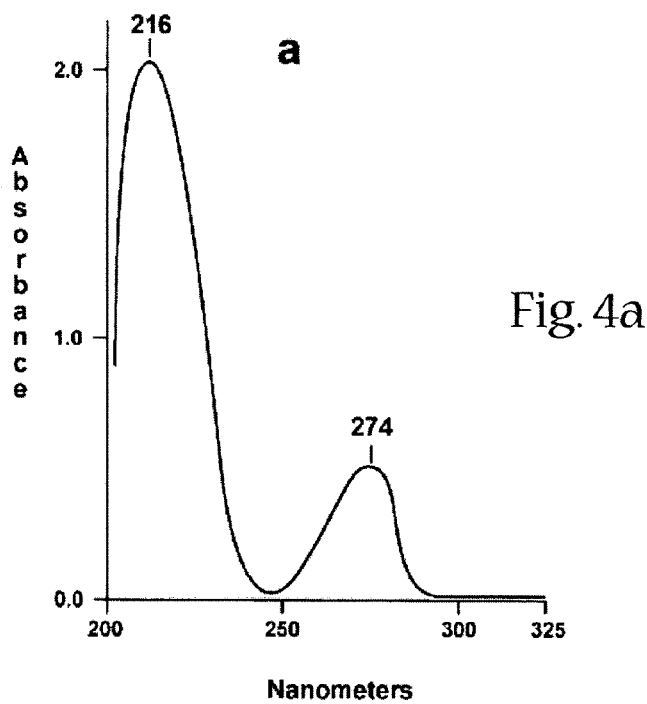
FIG. 4a is a UV spectrogram of propofol.
Figure 4B:
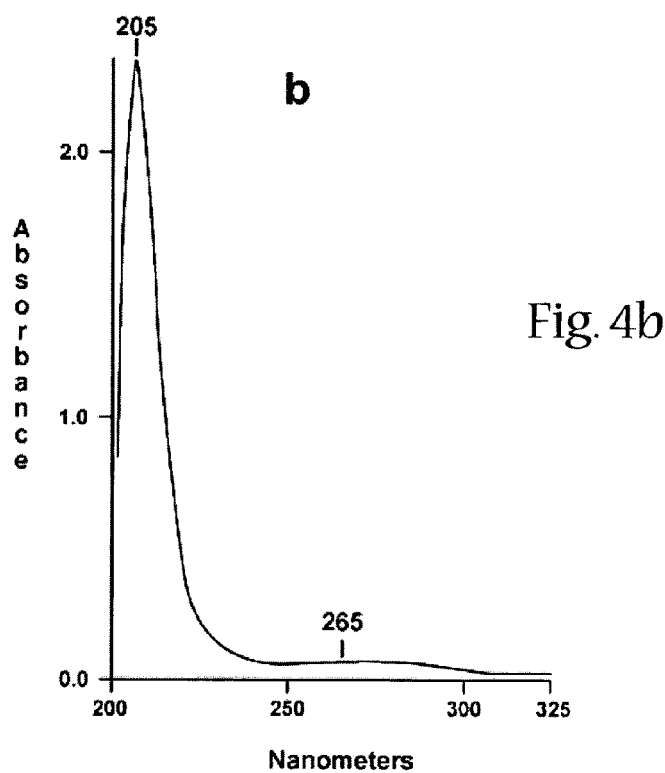
FIG. 4b is a UV spectrogram of the propofol-DHA conjugate from the reaction described in Example 2.

The propofol spectra showed two absorption peaks at 219 nm and 274 nm (FIG. 4a). These peaks were shifted to 214 nm and 260 nm (FIG. 4b) respectively for the new compound (propofol-DHA).

b) Gas Chromatography Analysis

Figure 5A:
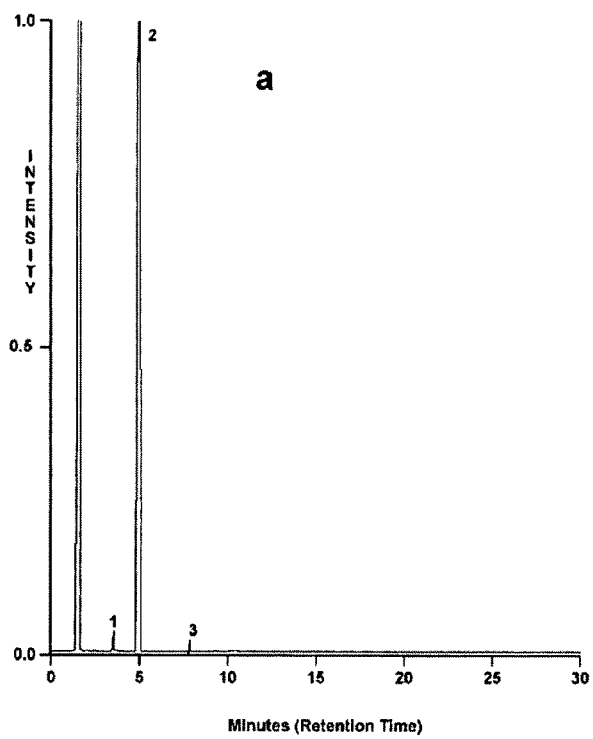
FIG. 5a is a spectrogram from the gas chromatographic analysis of propofol.
Figure 5B:
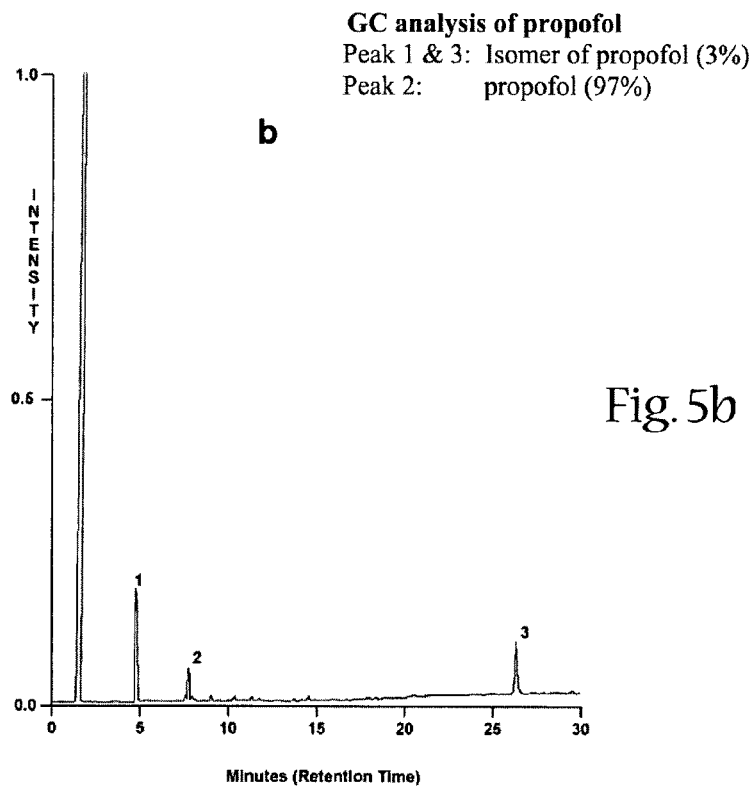
FIG. 5b is a spectrogram from the gas chromatographic analysis of the propofol-DHA conjugate from the reaction described in Example 2.

The propofol-DHA conjugate was hydrolyzed and then methylated for analysis by Gas Chromatography. The results illustrated in FIGS. 5a and 5b demonstrate that the commercially available propofol (Adrich-Sigma Chemical Co.) contained 97% of pure compound (2,6 diisopropylphenol) with a retention time of 4.89 min and 3% of other propofol isomers (See FIG. 5a). Analysis of the hydrolyzed product of propofol-DHA conjugate resulted in 50% yield of DHA (retention time 26.10), a 40% yield (retention time 4.89) of propofol (2,6 diisopropylphenol), and remaining a 10% yield of other isoforms of propofol (See FIG. 5b).

c) Infrared Spectra

Figure 6:
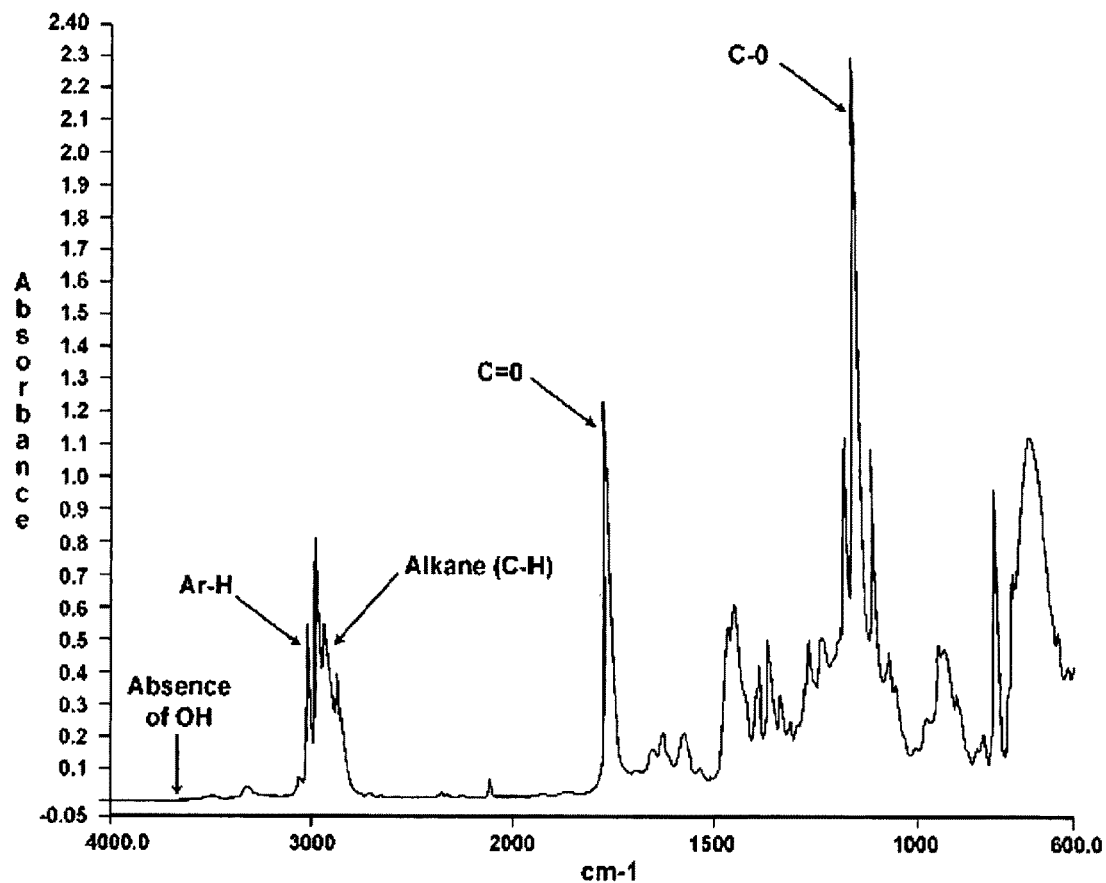
FIG. 6 is an infrared spectrogram of the propofol-DHA conjugate from the reaction described in Example 2.

The infrared absorption spectra of the propofol-DHA conjugate (See FIG. 6) showed two strong absorptions for characteristic ester group: a C=O stretch ($1750\ cm^{-1}$) and a C—C—O docosahexaenoate stretch ($1250\ cm^{-1}$). The spectra also show absorptions at $3000$-$3070\ cm^{-1}$, which are characteristic of the aromatic C—H stretch. These results further confirm formation of a propofol-DHA conjugate.

d) Mass Spectra

Figure 7:
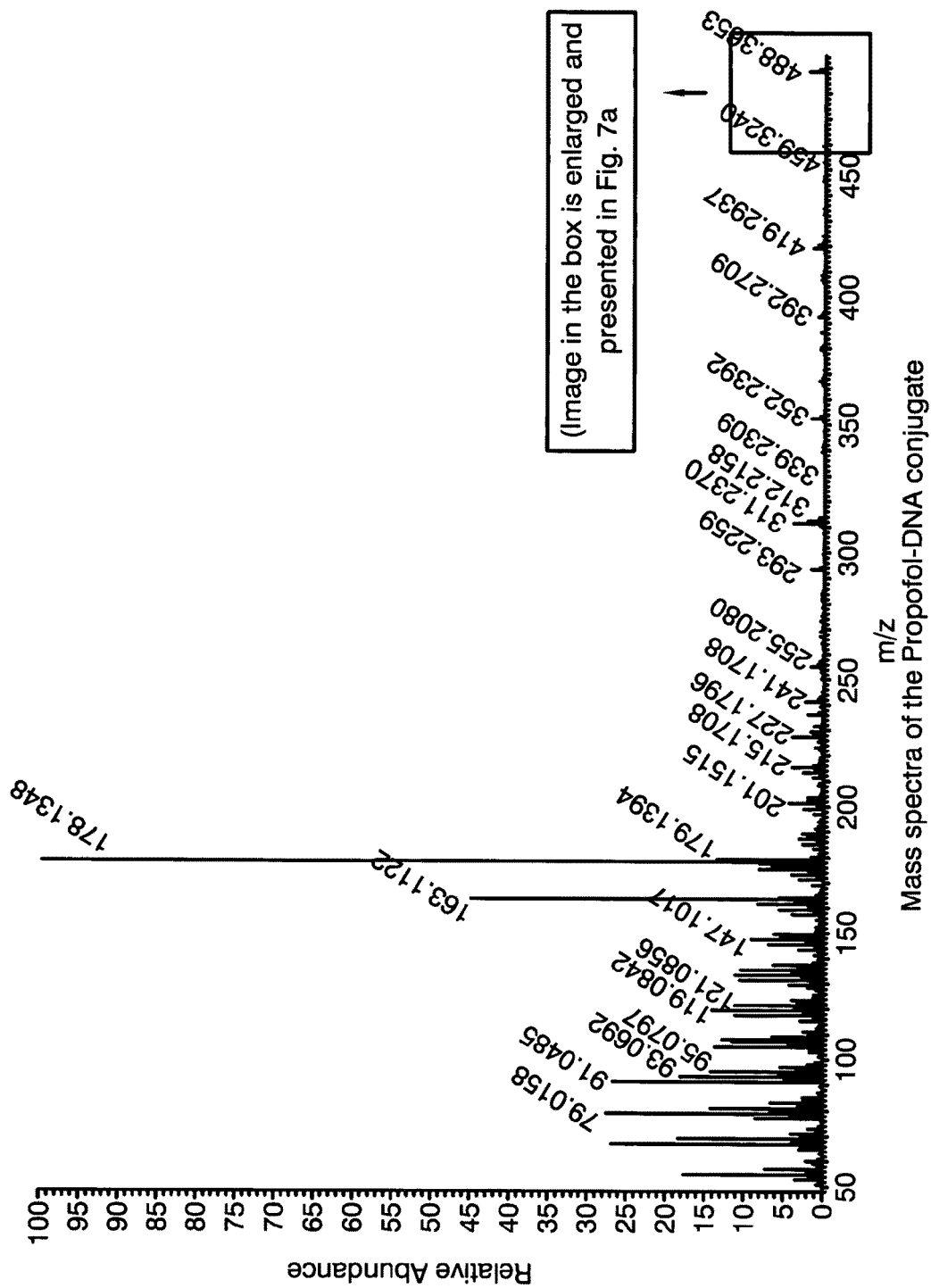
FIG. 7 is a mass spectrogram of the propofol-DHA conjugate from the reaction described in Example 2.

Mass spectroscopy was used to analyze the propofol-DHA conjugate (See FIG. 7). The mass spectra revealed a compound in the reaction mixture having a molecular weight of 489.3, which appeared to be very close to the calculated molecular weight of 488.85. A slight discrepancy in the molecular weight is due to protonization of product during mass spectrum analysis.

The analytical results described above indicate that esterification of DHA with propofol results in a pure propofol-DHA conjugated product.

Example 3

Synthesis, Purification and Characterization of 2,6-Diisopropylphenyl Eicosopentenoate (Propofol-EPA)

A propofol-EPA conjugate was also synthesized and characterized using similar synthetic and analytical approaches as those described above for the propofol-DHA conjugate.

Example 4

Effect of DHA and RVT on Jurkat Leukemic Cell Growth

Figure 8:
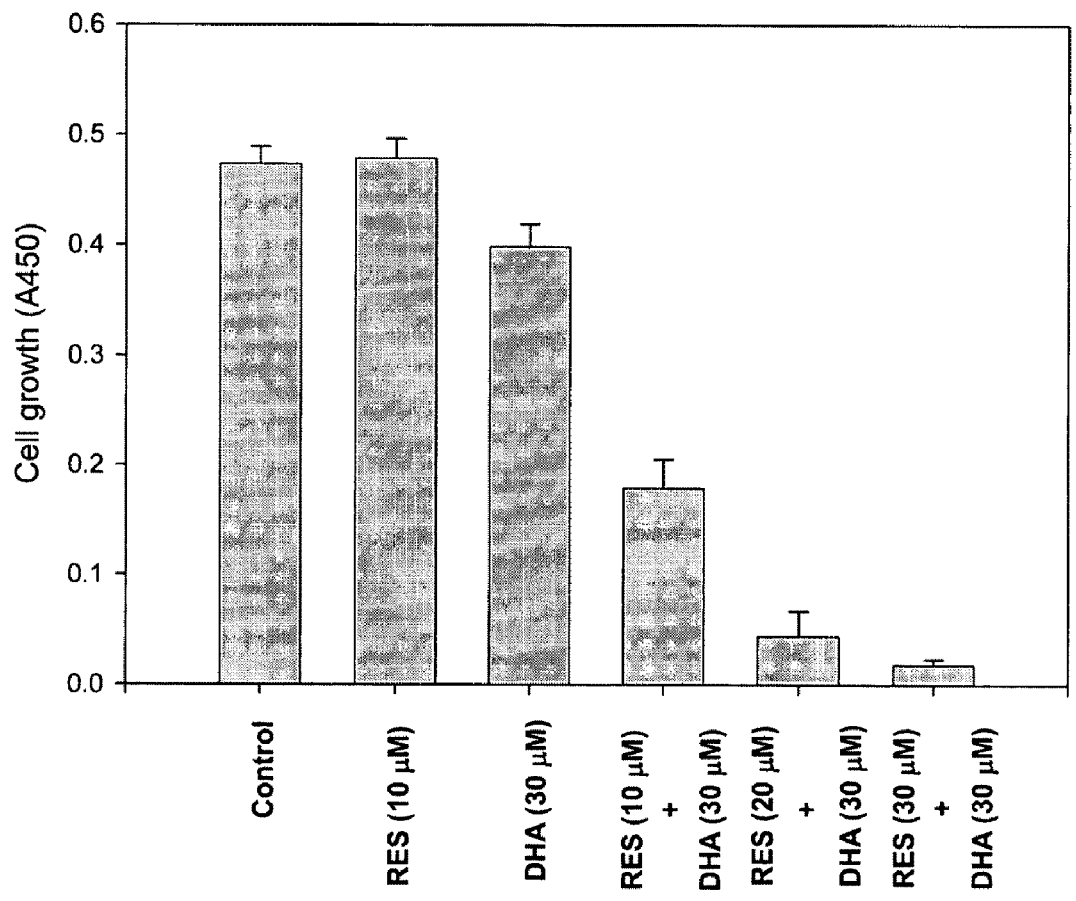
FIG. 8 is a bar graph illustrating the effect of resveratrol and docosahexaenoic acid on Jurkat cell growth.

In order to evaluate the anti-proliferative activity and synergism between DHA and RVT, the two compounds were added separately to cell cultures containing Jurkat leukemic cells. In a separate experiment, a mixture of DHA and RVT components were added to the Jurkat leukemic cell cultures. The results are illustrated in FIG. 8 as a bar graph. Jurkat cells (Jurkat clone E6-1 from American Type Culture Collection of Manassas, Va. ($5\times10^4$/well)) were incubated with either DHA or RVT, or a combination as indicated in a 96-well plate for 24 hours at 37° C. using a 5% $CO_2$ in RPMI media containing 2% serum. Cell growth and viability were determined using a WST-1 Cell Proliferation Kit (sold by Roche Molecular Biochemicals of Indianapolis, Ind.). The control was a "ethanol-treated" control group. For the results illustrated in FIG. 8, the average was taken of three separate experiments. For the combination of DHA and RVT, a student t test provided a $P<0.001$ relative to the "ethanol-treated" control group. The results indicate that neither the DHA (up to 30 μM) nor the RVT (10 μM) alone had any significant effect on Jurkat cell growth. However, when the two components were combined into a single formulation, a synergistic inhibition of Jurkat cell growth was observed. The combination of DHA (30 μM) and RVT (10 μM) inhibited cell growth by about 60%. This is indicative of a synergistic interaction between DHA and RVT on cancer cell growth. Furthermore, increasing the RVT concentration further enhanced the cytotoxic effect of the DHA.

Example 5

Evaluation of Cytoxicity of Polyphenolic Anti-Oxidants

Figure 9:
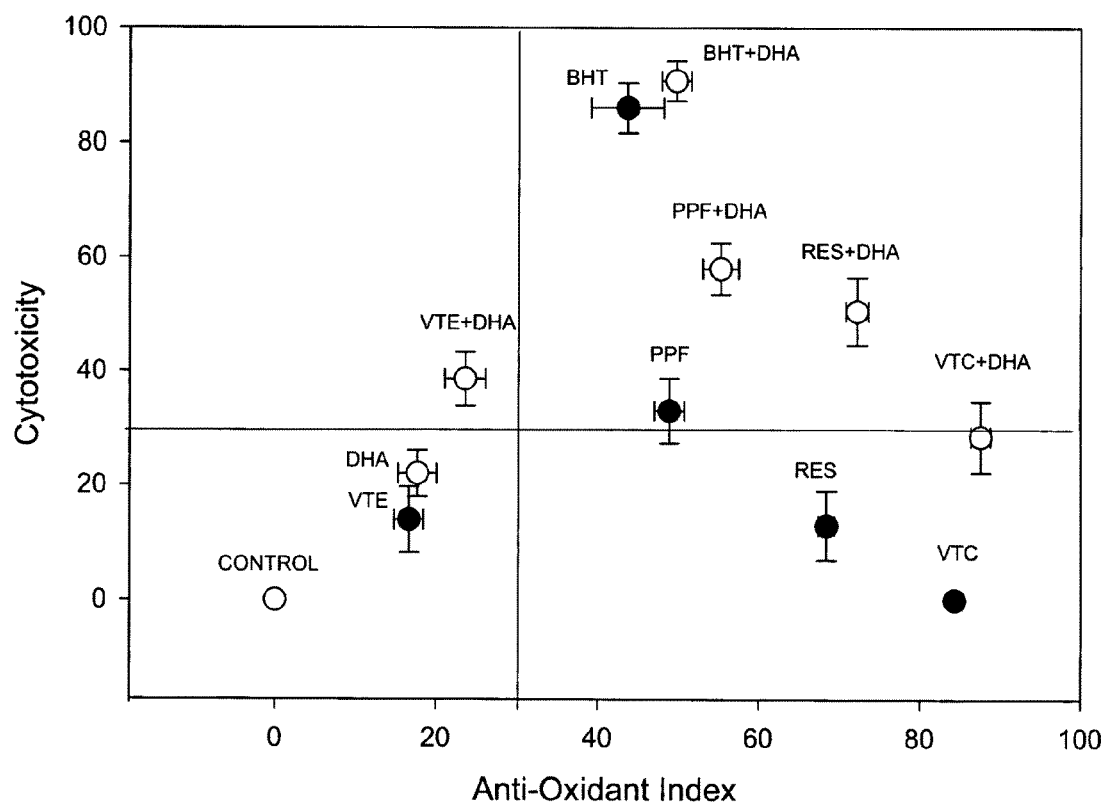
FIG. 9 is a plot correlating the anti-oxidant properties and the cytotoxic properties of several anti-oxidants.

Resveratrol (RVT) discussed above is a polyphenolic anti-oxidant. A number of different anti-oxidants were evaluated to consider whether there was a correlation of the anti-oxidation properties of these components and cell growth inhibition. The different anti-oxidants were selected to include those with and those without polyphenolic ring structures. The results of the evaluation are illustrated in FIG. 9.

The Jurkat cells were incubated in a 96-well plate ($5 \times 10^4$ cells/well). The wells were then treated with one of the following phenolic compounds: propofol (PPF, 25 μM), butylated hydroxytoluene (BHT, 10 μM), resveratrol (RVT 25 μM), vitamin E (VTE, 25 μM), and vitamin C (VTC, 25 μM) both in the presence and then in the absence of DHA (5 μM) for 2 hours at 37° C. at 5% $CO_2$ in a serum-free RPMI medium. The phenols PPF, BHT, RVT, and VTE were suspended in DMSO while the RTC was dissolved in the RPMI media. Control cells were treated with equal amounts of the appropriate vehicles (DMSO, ethanol, or both, or the RPMI media). Cell viability was determined using a WST-1 Cell Proliferation Kit (sold by Roche Molecular Biochemicals of Indianapolis, Ind.). The anti-oxidation index for each of the phenols was determined using 2,7-dichlorodihydrofluorescein diacetate (5 μM) according to the procedure described in Sanchez et al. *Anal. Biochem.* 1990, 187, 129-132 and LeBel et al. *Chem. Res. Toxicol.* 1992, 5, 227-231. The fluorescence intensity was due to the interaction of the free oxygen radicals with the dye and was measured at $\lambda_{ex}$ 495 nm and $\lambda_{em}$ 529 nm in a 96 well plate fluorescence reader. The cytotoxic index was calculated as the percentage of dead cells compared to the control. The anti-oxidation index was calculated as the percentage of fluorescence intensity reduction to that of the controls (vehicle treated cells). Review of the data in FIG. 9 indicates that there is not a strong correlation between the anti-oxidation properties and the cytoxicity of the tested phenols. Consequently, it is suggested that the anti-oxidation property is not necessarily responsible for the DHA-induced cytotoxic effects.

Example 6

Figure 10A:
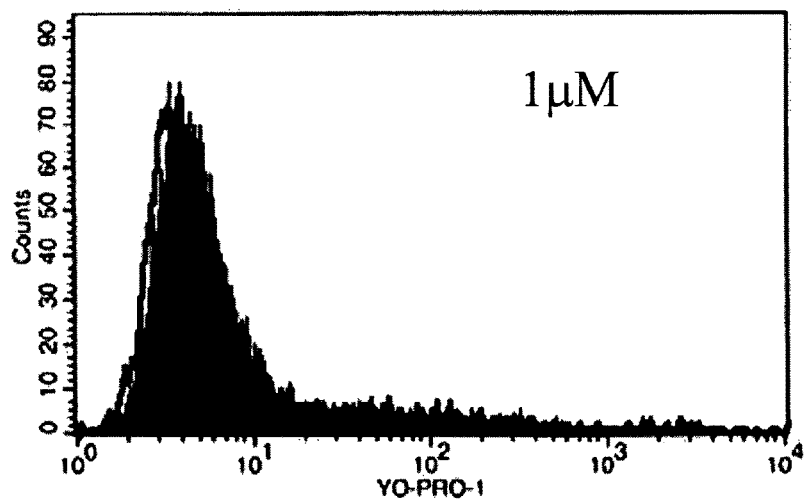
FIGS. 10a-c are histograms illustrating the effect of the resveratrol ester of docosahexaenoic acid on Jurkat leukemic cell apoptosis.
Figure 10B:
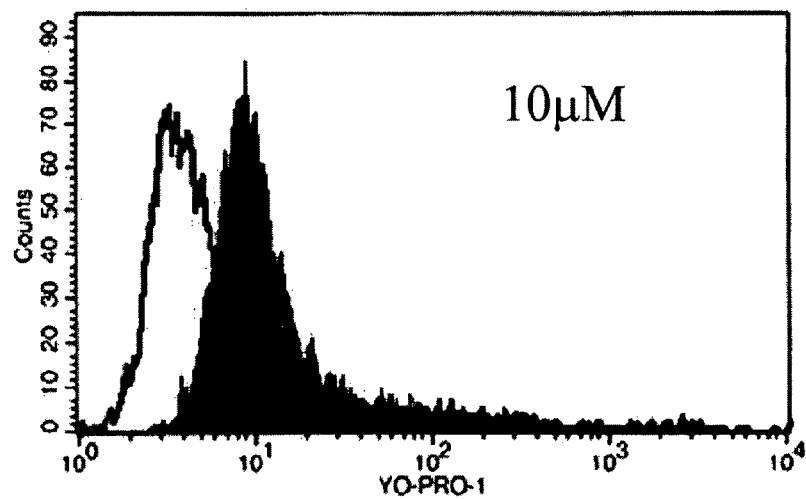
Figure 10C:
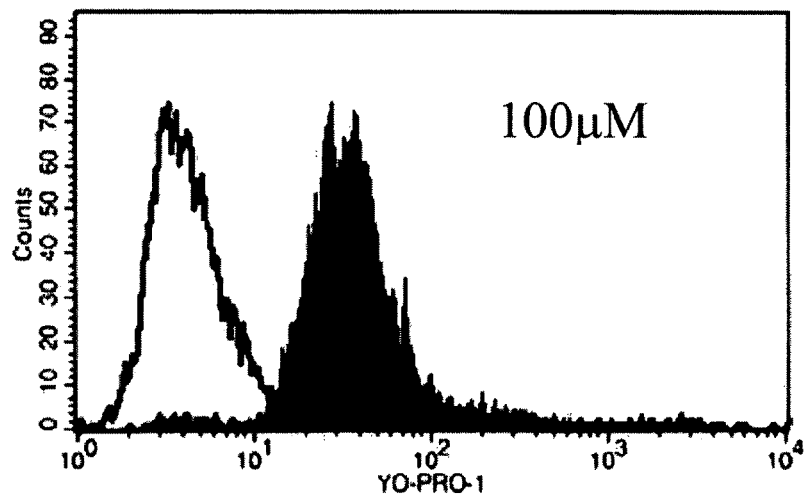

Effect of the Resveratrol Ester of Docosahexaenoic Acid on Jurkat Leukemic Cells Apoptosis The DHA-RVT ester prepared according to Example 1 was dissolved in DMSO. This solution was used to treat Jurkat cells labeled with YO-PRO-1 (sold by Molecular Probes of Oregon), which is a green fluorescent dye used in flagging apoptotic cells. The labeled cells were analyzed using a FACStar-plus flow cytometer equipped with a water-cooled argon laser emitting at a frequency of 488 nm. Detection of the fluorescent probe was ascertained using a 530±30 band-pass filter. The data depicted in FIGS. 10a-c are illustrated in the form of a histogram. The fluorescent intensity is indicative of apoptotic expression. The unfilled histogram represents the labeled, non-treated cells (1); the filled histogram represents the treated cells (2). The results indicate that a concentration of 10 μM of the DHA-RVT ester (FIG. 10a) produced apoptosis in nearly all of the Jurkat cells. At approximately 1 μM concentration, the DHA-RVT ester induced apoptosis in approximately 50% of the Jurkat cells (FIG. 10b) while at a concentration of 0.1 μM the ester had little effect on the Jurkat cells (FIG. 10c). Concentrations of resveratrol (10 μM) plus DHA (10 μM) have no effect on Jurkat cell growth.

Example 7

Biological Effects of Propofol-DHA and Propofol-EPA Conjugates

Figure 11:
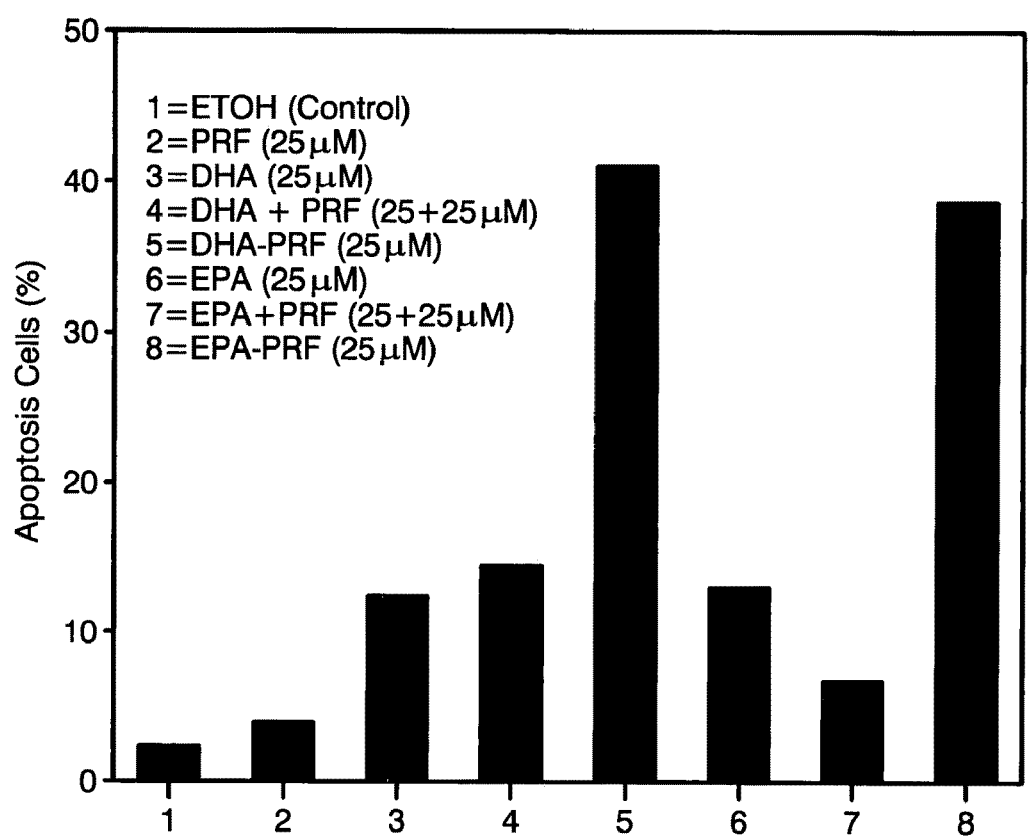
FIG. 11 is a bar graph illustrating the induction of apoptosis by DHA, EPA, alone or with propofol as additive or synthetic conjugate.
Figure 12:
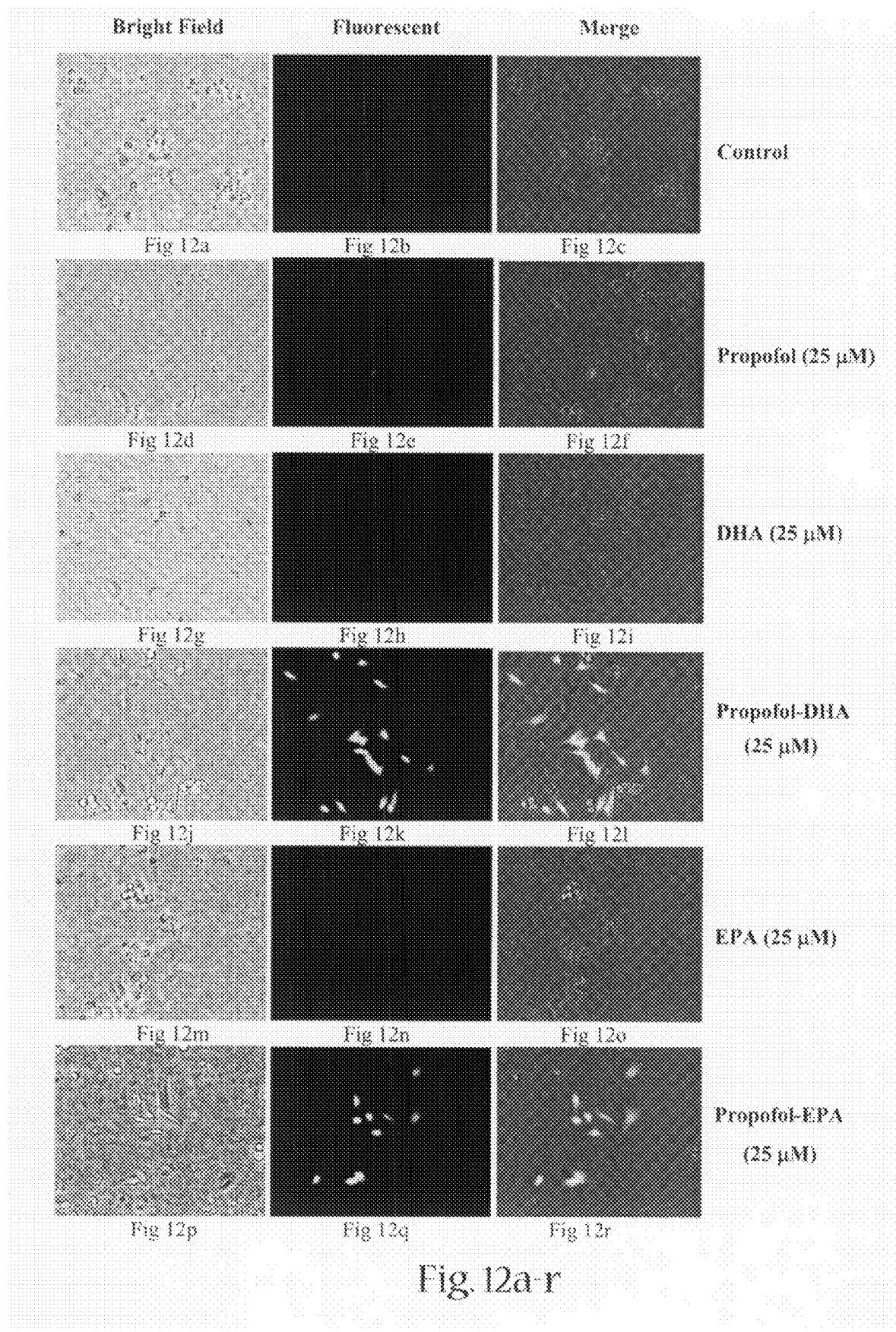
FIGS. 12a-12r are scanned images of fluorescent microscopy of apoptotic cells.

DHA and EPA conjugates of propofol are used to test their activities against MDA-231-MB breast cancer cells. Induction of apoptosis was assayed by incubating cells with DHA, EPA, or propofol alone or DHA, EPA with propofol as well as DHA-, and EPA as propofol conjugates for 4 hours at 37° C. After this incubation, a specific fluorescent caspase 3 inhibitor (FITC-DEVD-FMK) that binds specifically to activated caspase 3 was added, and FITC positive fluorescence was observed under the microscope. Results indicate that 25 μM DHA-propofol or EPA-propofol effectively induced apoptosis in these cells whereas similar concentrations of DHA, EPA or propofol or propofol with DHA or EPA were not very effective (FIG. 11). Representative pictures indicating apoptotic positive cells are shown in FIGS. 12a-12r.

Example 8

Cell Adhesion Assay

The cell adhesion assay was performed according to the procedure described in Deryugina, E. I., Ratnikov, B., Postnova, T. I., Rozanov, D. V., Strongin, A. Y. (2002) *J. Biol. Chem.* 277, 9749-9756. The cell adhesion assay was preformed using cyctomatrix of human vitronectin in a 96-well plate (Chemicon International Incorp. of Temecula, Calif.). Each well was incubated with 100 μL of breast carcinoma MDA-MB-231 cells ($1 \times 10^5$ cells/ml) at 37° C. for 45 min in a $CO_2$ incubator. Individual wells were treated with one of the following: (a) individual agents: DHA, EPA, and propofol; or (b) the combined agents: DHA and propofol, and EPA and propofol; or (c) the conjugates DHA-propofol, or EPA propofol (prepared as described above in Examples 2 and 3). After incubation, the wells were washed three times with PBS, and the adhered cells were stained with crystal violet in 10% ethanol for 5 min at room temperature. The excess stain was subsequently removed by washing the wells six times with PBS. The stained cells were dissolved in 100 microliters (μL) of solubilizing buffer (1:1 mixture of 0.1M $NaH_2PO_4$ at a pH of 4.5 in 50% ethanol) and the absorbance of each of the resulting samples was read at 540 nm. The absorbance of dye in the control (vehicle treated cells) was regarded as 100%, and the percent adherence of treated cells was calculated in comparison to that control. The results are graphically displayed in FIG. 13.

Figure 13:
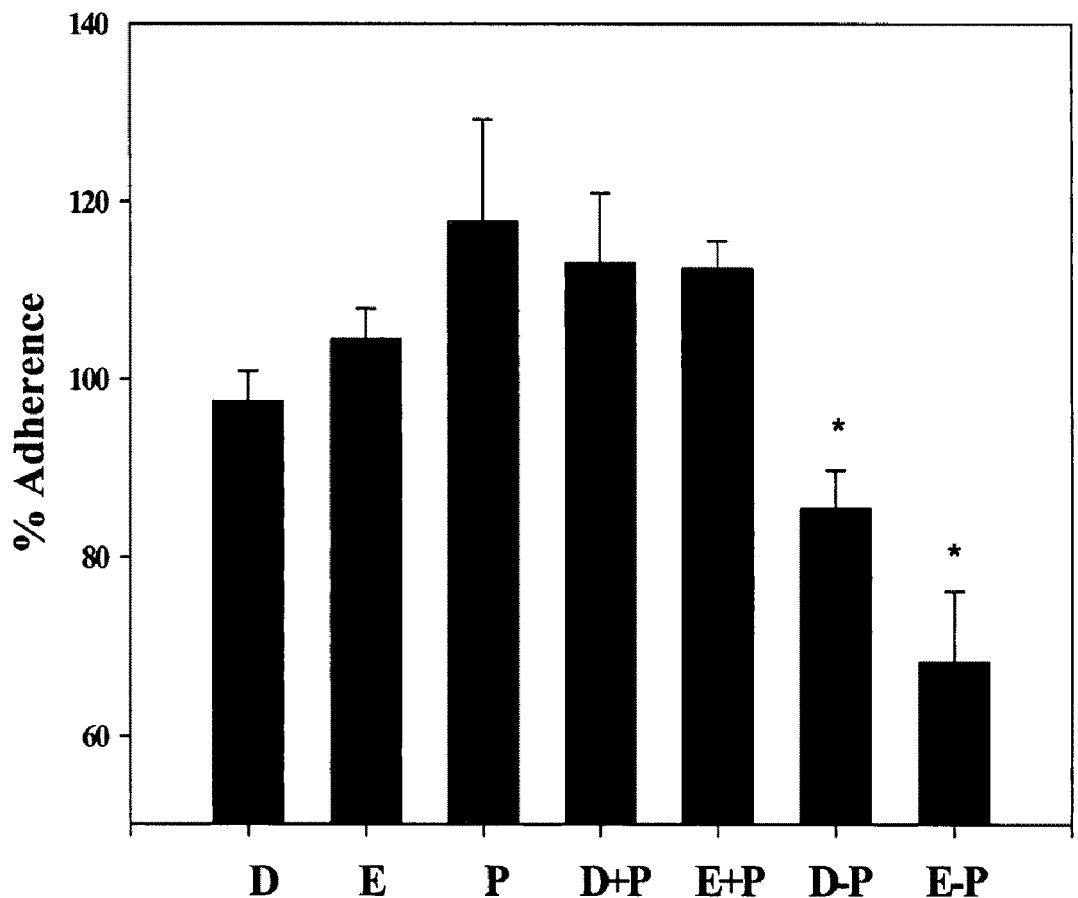
FIG. 13 is a bar graph illustrating the percent adherence of cells from breast cell line MDA-MB-231 to vitronectin.

The results illustrated in the bar graph of FIG. 13 indicate that the two conjugates, DHA-propofol and EPA-propofol possess unique biological properties including the inhibition of adherence of cancerous cells to connective tissue, vitronectin, that is not displayed by either the individual agents, DHA, EPA or propofol or by the simple combination of these agents.

What is claimed is:

1. A method of treating mammalian cells, the method comprising administering to the cells a pharmaceutical formulation comprising a phenolic ester of a fatty acid in an amount effective to induce cytotoxicity in at least a portion of the cells.

2. The method of claim 1 wherein the mammalian cells are tumor cells.

3. The method of claim 1 wherein the fatty acid is ω-3 long chain unsaturated or polyunsaturated fatty acid.

4. The method of claim 1 wherein the fatty acid is selected from the group of fatty acids consisting of: lauric acid, myristic acid, palmitic acid, stearic acid, arachidic acid, behenic acid, lignoceric acid, palmitoleic acid, oleic acid, linoleic acid, linolenic acid, and arachidonoic, docosahexanoic acid, and eicosopentenoic acid.

5. The method of claim 1 wherein the phenol is a polyhydric phenol or a polynuclear phenol.

6. The method of claim 1 wherein the phenol is selected from the group consisting of: resveratrol, quercetin, catechin, propofol, and genistein.

7. The method of claim 1 wherein the phenol is selected from the group of phenols consisting of resveratrol, catechins, flavonoids, and alpha-tocopherol.

8. A method of treating mammalian cells, the method comprising:
    administering to the cells a pharmaceutical formulation comprising a phenolic ester of a fatty acid in an amount effective to modulate cell injury or cell dysfunction or both.

9. A method of inhibiting metastasis of malignant tumor cells or a malignant growth in a mammal, said method comprising administering to the mammal a pharmaceutical formulation comprising an effective amount of a phenolic ester of a fatty acid in a pharmaceutically acceptable carrier to inhibit the tumor cell or malignant growth from metastasizing to a secondary tissue site.

10. The method of claim 9 wherein the fatty acid is a polyunsaturated fatty acid.

11. The method of claim 9 wherein the fatty acid is an ω-3 long chain polyunsaturated fatty acid.

12. The method of claim 9 wherein the fatty acid is selected from the group consisting of: lauric acid, myristic acid, palmitic acid, stearic acid, arachidic acid, behenic acid, lignoceric acid, palmitoleic acid, oleic acid, linoleic acid, linolenic acid, and arachidonoic, docosahexanoic acid, and eicosopentenoic acid.

13. The method of claim 9 wherein the phenol is a polyhydric phenol or a polynuclear phenol.

14. The method of claim 9 wherein the phenol is selected from the group consisting of: resveratrol, quercetin, catechin, propofol, and genistein.

15. The method of claim 9 wherein the phenol is selected from the group consisting of: resveratrol, quercetin, catechin, propofol, and genistein.

16. The method of claim 9 wherein the pharmaceutical formulation inhibits the tumor cell or malignant growth from metastasizing to a secondary tissue site, said secondary site involving connective tissue within the mammal.

17. A method of treating mammalian cells, the method comprising administering to the cells a pharmaceutical formulation comprising a histidyl conjugate of a fatty acid in an amount effective to modulate cell injury or cell dysfunction or both.

* * * * *